(12) United States Patent
Houard et al.

(10) Patent No.: US 9,421,078 B2
(45) Date of Patent: Aug. 23, 2016

(54) IMPLANTABLE PLATE FOR RECONSTRUCTION OF WALLS

(75) Inventors: William Houard, Labastide Rouairoux (FR); Walter Bertolaso, Montauban (FR)

(73) Assignee: TEXTILE HI-TEC (T.H.T.), Verreries de Moussans (FR)

(*) Notice: Subject to any disclaimer, the term of this patent is extended or adjusted under 35 U.S.C. 154(b) by 937 days.

(21) Appl. No.: 13/147,026

(22) PCT Filed: Sep. 4, 2009

(86) PCT No.: PCT/FR2009/001066
§ 371 (c)(1),
(2), (4) Date: Sep. 9, 2011

(87) PCT Pub. No.: WO2010/086515
PCT Pub. Date: Aug. 5, 2010

(65) Prior Publication Data
US 2012/0016388 A1   Jan. 19, 2012

(30) Foreign Application Priority Data
Jan. 30, 2009   (FR) .................................. 09 50600

(51) Int. Cl.
*A61F 2/02* (2006.01)
*A61F 2/00* (2006.01)
*D04B 21/12* (2006.01)

(52) U.S. Cl.
CPC ............ *A61F 2/0063* (2013.01); *D04B 21/12* (2013.01); *A61F 2250/0098* (2013.01); *D10B 2403/0213* (2013.01); *D10B 2509/08* (2013.01)

(58) Field of Classification Search
CPC ..................... A61F 2/0063; A61F 2250/0098; D10B 2403/0213
USPC ........................................ 623/23.72; 606/213
See application file for complete search history.

(56) References Cited

U.S. PATENT DOCUMENTS 2,464,301 A * 3/1949 Francis, Jr. .................. 428/167
4,769,038 A    9/1988 Bendavid et al.
(Continued)

FOREIGN PATENT DOCUMENTS

| EP | 0 719 527 A | 7/1996 |
|---|---|---|
| EP | 0 836 838 A | 4/1998 |
| EP | 1 384 450 A | 1/2004 |
| EP | 1 567 205 B1 | 8/2005 |
| FR | 2 712 177 A | 5/1995 |
| FR | 2 776 179 A | 9/1999 |
| FR | 2 914 179 A | 10/2008 |
| WO | 03/026530 A | 4/2003 |
| WO | 03/099160 A | 12/2003 |
| WO | WO 03099160 A1 * | 12/2003 |
| WO | 2004/052423 A | 6/2004 |

OTHER PUBLICATIONS

International Search Report & Written Opinion mailed Nov. 26, 2009 of PCT/FR2009/001066.

*Primary Examiner* — Gregory Anderson
*Assistant Examiner* — Christina Lauer
(74) *Attorney, Agent, or Firm* — Kenyon & Kenyon LLP

(57) ABSTRACT

The implantable plate for wall reconstruction comprises a textile support having anti-migratory protuberances on at least one face.
If the support comprises thermoplastic fibers or filaments, each protuberance is formed with a conical configuration, by swaging, inside a peripheral zone in which said fibers or filaments are thermowelded, especially by ultrasound, a perforation being centered relative to the peripheral zone.
The two faces can comprise protuberances, of a height substantially equal to the thickness of said support, for example distributed in a stagger and alternating from one face to the other, at the rate of 0.5 to 2 per $cm^2$.
The plate can comprise radio-opaque marking in the form of lines passing between the protuberances to constitute a grid.

20 Claims, 3 Drawing Sheets

(56) References Cited

Figure 1:
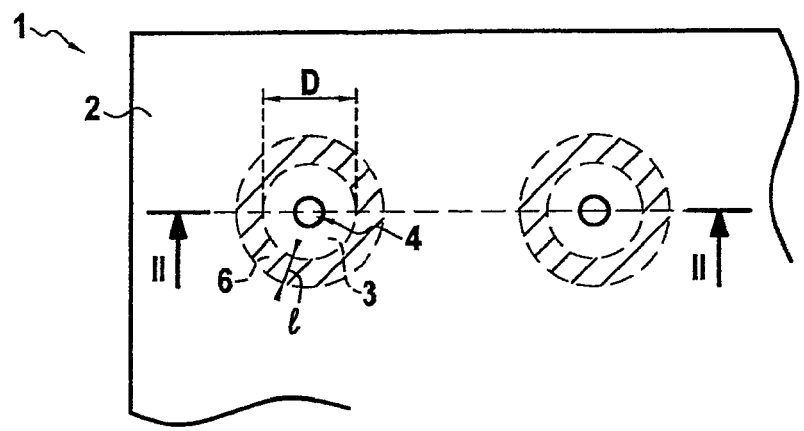

U.S. PATENT DOCUMENTS 5,676,967 A * 10/1997 Williams et al. ............. 424/443
5,990,378 A * 11/1999 Ellis .......................... 623/11.11

2002/0133227 A1 * 9/2002 Murphy et al. ................ 623/3.1
2003/0040809 A1 * 2/2003 Goldmann et al. ........ 623/23.76
2007/0250147 A1 10/2007 Walther et al.

* cited by examiner

IMPLANTABLE PLATE FOR RECONSTRUCTION OF WALLS

This is a 371 national phase application of PCT/FR2009/001066 filed 4 Sep. 2009, claiming priority to French Patent Application No. 0950600 filed 30 Jan. 2009, the contents of which are incorporated herein by reference.

The present invention relates to a prosthetic plate, specifically a plate which is implantable for the reconstruction of walls, especially in the treatment of hernias.

In the surgical domain, the term plate is used to generally designate a supple piece, made of biocompatible and generally porous material, a piece which is used for manufacturing a prosthesis, especially one designed to reinforce a defective wall. The prosthesis per se can be made from a single plate, as in document FR 2 712 177, or from two plates, as in documents U.S. Pat. No. 4,769,038 and EP 0 836 838 or even three plates, as in document EPA 0 719 527. The plate per se can be formed from a single layer, especially a single-thickness tissue, as in document FR 2 712 177 or can be composed from several layers, as in document EP 1 567 205.

For the prosthesis to be fully effective, it is important that it remain in place in the position it was given during its implantation. To achieve this, the practitioner fixes the prosthesis onto surrounding structures by means of staples or sutures, as in document U.S. Pat. No. 4,769,038. This fixing, which is done under tension, can cause an unpleasant sensation for the patient, or even pain during certain movements. Also, placing staples or sutures prolongs the duration of an operation by the surgeon to correctly position the prosthesis. Also, the staples or the sutures can be a source of inflammation.

Document FR 2 776 179 discloses a composite surgical plate which comprises a smooth internal layer and a rough external layer, the roughness of said layer purported to allow hooking of organic tissues to compensate for the effects of glide relative to the plate and adjacent tissues. In this document FR 2 776 179, the external layer is preferably a layer of non-woven fibrillar textile, especially comprising threads of polyamide or biocompatible polypropylene. This document specifies that such an external layer allow good colonisation by the organic tissues in contact with the plate.

But the applicant believes that the simple structure of the external layer, specifically a non-woven fibrillar structure, is not capable of preventing displacement of the plate in the period following implantation and preceding tissular colonisation.

The aim of the present invention is to propose an implantable plate for the reconstruction of walls which rectifies the drawbacks of the abovementioned plates both in that it requires no fixing by stapling or suturing and also reliably ensures that the prosthesis is held in place in the period following implantation of said prosthesis by the surgeon.

Document WO 03/099160 A1 describes a medical implant which comprises an embossed film optionally linked to a base structure which can be textile. It is mentioned in this document that the bossing formed in this film can be designed to increase or reduce friction of the implant in the body, which can be used either for fixing the implant or for increasing its mobility. But there is no indication given as to the particular structure of the film which produces such increase or reduction in friction.

As is known, the implantable plate of the present invention comprises a textile support and has protuberances. It is characterised in that the protuberances are formed in the textile support itself, on at least one of its faces. So, according to the particular arrangement of the present invention, when the plate is implanted, the face of the textile support which comprises the protuberances comes into contact with the organic tissues and the protuberances which are constituted by the fibres or filaments of the textile support form so many friction zones between the plate and said tissues, creating friction forces preventing displacement of said plate relative to said tissues.

In a preferred embodiment, the protuberances have a conical configuration, such configuration making it easy for penetration of the protuberances into the organic tissues. But this configuration is not exclusive, as the protuberances can especially have an undulating or cylindrical form.

According to a variant embodiment, the textile support comprises perforations which are principally intended to favour drainage body fluids and optionally favour tissular colonisation in the event where the structure itself of the textile support is not sufficiently open. These perforations are preferably placed at the level of the protuberances such that the contours of the perforation form ridges which boost the friction effect of the actual protuberance.

When the protuberance preferably has an axis of symmetry, the perforation is an orifice centred on this axis. Therefore, in the event where the protuberance has a conical configuration, the presence of the perforation actually shows that the protuberance has a form of a frustum.

In a preferred variant embodiment, the textile support comprises at least in part thermoplastic fibres or filaments and each protuberance is formed in a determined zone of the textile support by deformation of the structure of the support and by thermowelding of at least some of said fibres or filaments of said zone. For example, the protuberance can be formed inside a peripheral portion, especially annular, of said zone in which said fibres or filaments are thermowelded. Thermo-welding of fibres or filaments making up the peripheral portion ensures that said portion has a certain rigidity, forming the protuberance by pushing back to the exterior of the plane of the textile support and thus deforming the structure of the textile support, formed by fibres or filaments not thermowelded, which is located inside said peripheral portion.

When the textile support preferably comprises perforations, these are centred relative to the peripheral portion of the determined zone.

However, the protuberance is preferably formed by deformation and by thermowelding of all the fibres or filaments of the determined zone of the textile support. For example, deformation occurs by swaging between two complementary tools, male and female, having the preferred configuration for the protuberance and thermowelding occurs by application using the same tools of treatment for conducting thermowelding of fibres or filaments deformed during swaging. In this case there is, in the first instance, deformation of the initial structure of the textile support, especially displacement of fibres or filaments relative to one another to the point where the preferred configuration for the protuberance is produced, and in the second instance there is thermowelding of fibres or filaments in their new arrangement. The at least superficial fusion of the fibres or filaments developed during the thermowelding operation lends certain rigidity to the assembly of fibres or filaments of the protuberance, in turn strengthening its frictional properties and thus the anti-migratory character of the plate.

Thermo-welding of the fibres or thermoplastic filaments is done especially by ultrasound.

According to a variant embodiment, the textile support is a non-woven material which is thermo-bonded at points.

According to another variant embodiment, the textile support is a tissue of 3D or three-dimensional type, comprising two layers joined by connecting threads. This more widely varies the characteristics of the textile support, especially its thickness, the choice of the constituent components and its porosity. It can be made either by weaving or by knitting.

Weaving produces it by superposition of a sheet of warp threads and several sheets of weft threads or by superposition of several sheets of warp threads and weft threads. The bond of these different sheets is ensured either by some of the warp threads of at least one of the sheets of the superposition warp threads or by a supplementary sheet of warp threads, a so-called chain warp.

Knitting produces it on a double-bed tricot machine, in which bonding of the two respectively knitted layers on each bed is ensured by a supplementary sheet of chain which works alternatively on one and the other beds.

According to a variant embodiment, at least some protuberances comprise openings capable of allowing cellular colonisation of the implant at the level of said protuberances and also drainage of body fluids, preventing perforations from forming in the textile support.

When the protuberances are formed by pushing back the fibres or filaments constituting the textile support, during this operation this results in relative displacement of some of the fibres or of some of the filaments likely to create openings in at least some protuberances. The presence or not of one or more openings in a protuberance, the size and configuration of each opening are fairly random parameters since they depend not only on the more or less open structure of the textile support but also on the placement, on the textile support, of the zone where the tools creating the protuberance act locally. If the structure of the textile support is relatively closed and if the tools act in a zone where there is major density of fibres or filaments, the protuberance could not contain an opening. On the contrary, the protuberance will be open if the structure of the textile support is itself open and if the tools act in a zone already comprising at least part of an opening.

To increase the probability of having open protuberances, a three-dimensional tissue obtained by knitting is preferably selected as a textile support, as mentioned hereinabove, which has an open, more pronounced character and this open character is controlled more easily than that obtained by weaving.

According to the relevant application, the plate of the present invention can have protuberances on a single face or on both faces.

In a particular embodiment, on the two faces of the textile support the plate comprises protuberances whereof the height is substantially equal to or greater than the thickness (e) of said support, preferably less than three times said thickness, especially of the order of twice said thickness. If the thickness exceeds three times the thickness of the textile support there is the risk of aggressiveness of the fibres or filaments constituting said protuberances.

These protuberances are preferably distributed uniformly, in a stagger and alternating from one face to the other, at the rate of 0.5 to 2 protuberances/cm$^2$. In a precise embodiment of protuberances formed by swaging inside an annular zone in which the thermoplastic fibres or filaments of the textile support were thermowelded by ultrasound, the annular zone had an inner diameter of the order of 2 to 5 mm and a width of the order of 0.5 mm.

According to a variant embodiment, the textile support is impregnated for example with collagen which favours cellular colonisation or polyurethane, said impregnation being capable of giving the plate a certain shape memory. The aim is to ensure that the plate may be wound up on itself for introduction into a trocar and to be deployed spontaneously when freed from the trocar.

According to a variant embodiment, the textile support comprises on one of its faces an anti-adherent coating, in particular on the face having no anti-migratory protuberances. Anti-adherent coating means a coating which is capable of preventing or at the very least considerably limiting adherence between the plate and the parts of the body against which it comes into contact, once implanted, especially the viscera. This can be a coating of collagen, polysaccharide or other biopolymer, resorbable or not.

Implantation of any prosthesis at all must be able to be the object of follow-up by the surgeon, so as to verify the performance of the prosthesis over time. In document FR 2 712 177 the prosthesis comprises tissue of single thickness resulting from weaving or knitting of multistrand polyester threads to form an open structure with square or rectangular mesh. To boost the rigidity of this prosthesis while constituting a radiological repair, the polyester threads are combined into a chain and/or a weft with metallic threads. The presence of these metallic threads therefore monitors the performance of the prosthesis during periodic radioscopic checks.

But the presence of metallic threads in the prosthetic plate can be a disadvantage, especially because it increases the rigidity of the latter and raises manufacturing costs. Also, it is hardly feasibly to introduce metallic threads to a structure other than woven or knitted. To rectify these disadvantages, the prosthetic plate of the present invention comprises radio-opaque marking on all or part of the surface of the textile support.

In a variant embodiment, this radio-opaque marking results from localised impregnation of the textile support by a silicon composition comprising a radio-opaque charge, especially a charge of barium or tantalum sulphate.

According to an embodiment, the marking is in the form of lines to form a regular grid.

In a precise and preferred example, the pitch of the grid is between 2 and 45 mm, preferably of the order of 15 mm.

Figure 2:
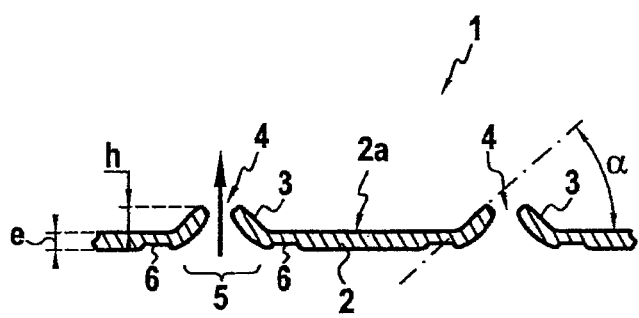
Figure 3:
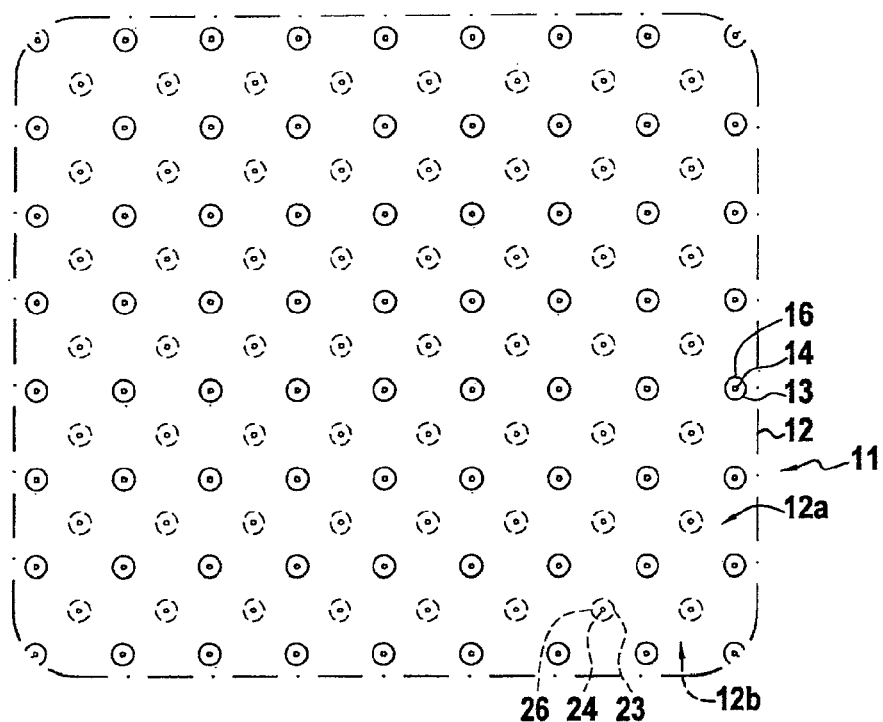
Figure 4:
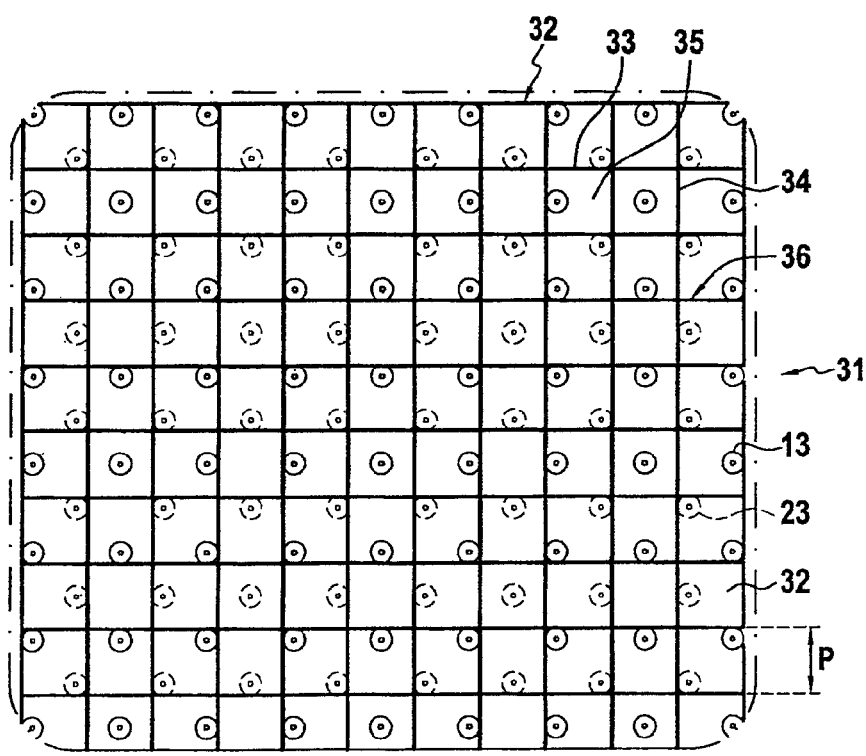
Figure 5:
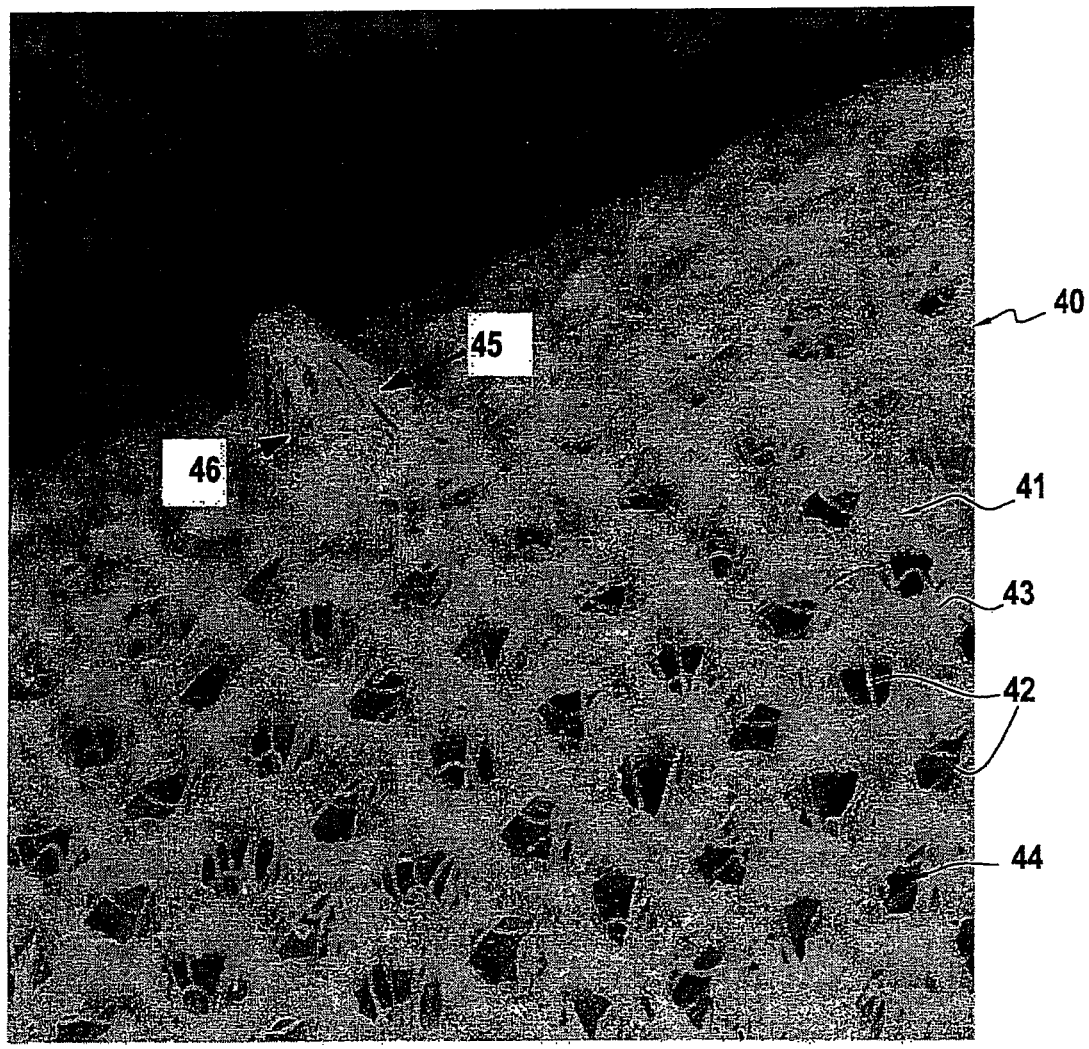

The present invention will be better understood from the description of embodiments of a prosthetic plate comprising anti-migratory protuberances, illustrated by the attached design, in which:

FIG. 1 is a schematic representation in plan view of a portion of a prosthetic plate comprising two truncated protuberances, FIG. 2 is a sectional schematic representation of the prosthetic plate of FIG. 1 according to the plane II-II, FIG. 3 is a schematic representation in plan view of a prosthetic plate having protuberances in relief on its two faces, FIG. 4 is a schematic representation in plan view of the plate of FIG. 3 comprising radio-opaque marking in the form of a grid passing between the protuberances, and FIG. 5 is a photograph taken by microscope illustrating a protuberance formed in a three-dimensional knitted fabric.

In general according to the invention, the prosthetic plate 1, designed for reconstruction of walls especially in the domain of hernias, comprises a textile support 2 whereof at least one of the faces 2a is surmounted by anti-migratory protuberances 3 formed from fibres or filaments composing the textile support itself.

These are the fibres or filaments which, coming into direct contact with organic tissues, impart to said protuberances an anti-migratory effect, preventing migration of the plate 1 once the latter has been implanted by the surgeon without being fixed in any manner, whether by mechanical means such as staples or suture threads or by any other means.

In the first example just described the textile support 2 is a non-woven material, formed by the interlocking of fibres or thermoplastic filaments which are joined together by bonding, more precisely by thermobonding by points, obtained by passing a sheet of fibres or filaments between two etched heating cylinders. This is in particular a non-woven material of 45 to 100 g/m$^2$, made from filaments of polypropylene. In this example the bonding has a density of 36 points/cm$^2$, each point being of the order of 0.1 mm$^2$.

In the embodiment illustrated in FIGS. 1 and 2, each protuberance 3 has the form of a frustum, the small open base of the frustum corresponding to a perforation 4, that is, a discharging hole, formed in the textile support 2. The angle $\alpha$ of inclination of the frustum, relative to the general plane of the textile support 2, is of the order of 45° in the example illustrated in FIG. 2. This value is not limiting. In the event where this angle $\alpha$ is 90°, the protuberance then has a configuration which is no longer truncated but cylindrical. Other configurations are naturally possible as long as this configuration and the number of protuberances achieve the preferred result, specifically of creating on the surface 2a of the textile support 2 so many points of friction increasing the friction coefficient between the plate 1 and the organic tissues against which the face 2a of the plate 1 is applied when the latter is implanted.

The protuberances 3 could optionally be formed during production of the textile support 2. But by way of simplification they are formed on the textile support already made by pushing back the fibres or filaments constituting said support 2 in a localised zone 5 to the exterior according to arrow F of FIG. 2.

In a precise embodiment, this localised zone 5 has been circumscribed by a peripheral portion, especially annular 6, in which the fibres or filaments constituting the textile support 2 have been thermowelded, especially by ultrasound. Therefore the fibres or filaments which are thermowelded in said portion 6 do not tend to move when the non-thermowelded fibres or filaments which are inside this peripheral portion 6 are pushed back according to arrow F. The thermo-welding lends some consolidation to the textile support about each protuberance 3. This, consolidation effect, allowing only the fibres or filaments of the localised zone 5 to move to form the protuberance 3, happens irrespective of the form of the peripheral zone, whether the latter has the form of a ring as in the illustrated example, or any other form.

Configuration of the protuberance 3 in this case is a function of the tool acting as slabbing or swaging of the textile support 2 in the localised zone 5. As indicated hereinabove, this configuration can be truncated as in the illustrated example, cylindrical, or even conical if there is no perforation 4, or may even be undulating, forming a wave effect not having an axis of symmetry as for the truncated, conical or cylindrical configurations but a plane of symmetry.

The function of the perforations 4, made in the textile support 2, is first to both facilitate drainage of body fluids coming into contact with the plate and the tissular colonisation of the plate, in particular when the latter has a microporous structure, as is the case for a thermo-bonded non-woven. It is this colonisation which produces definitive fixing of the plate 1 in a period which is generally a fortnight following implantation. The second function of these perforations is to increase, by the ridges they form when placed at the level of the protuberances 3, so many complementary friction points, contributing to the anti-migratory effect of the protuberances themselves.

The prosthetic plate 1 of FIG. 1 is formed for example in two successive steps. Starting out from a large-size textile support the first step consists of two simultaneous operations of cutting and perforation by swaging. The cutting operation gives the plate 1 its outer dimensions, for example a rectangle of 17 cm×15 cm. The perforation operation makes as many discharging holes as perforations 4 as wanted both in number and dimension, for example circular perforations of the order of 1 to 2 mm in diameter, at the rate of 0.5 to 2 perforations/cm$^2$. The second step consists of two simultaneous thermowelding operations by ultrasound according to the annular portion 6 and slabbing of the textile support inside this annular portion 6. These two operations require the use of an ultrasound tool comprising a male part and a female part. The prosthetic plate is placed on the female part. The male part comprises as many unitary sonotrodes as perforations, each unitary sonotrode supported on the prosthetic plate in the annular portion and comprising a central elongation forming a slabbing terminal piece. The prosthetic plate 2 is placed on the female part such that each perforation 4 is centred relative to a unitary annular sonotrode and at its slabbing terminal piece. During application of the male part on the female part, the unitary sonotrodes carry out localised fusion of the fibres or filaments of the prosthetic prosthesis in the annular portion 6 and the slabbing terminal piece deforms the structure of the textile support located inside this annular portion 6, shifting the non-thermowelded fibres or filaments to form the protuberances 3.

In the illustrated example in FIG. 2 the height h of each protuberance is substantially of the order of the thickness e of the prosthetic plate 2. In practice this height h is preferably of the order of twice this thickness e, normally not being greater than three times this thickness e to avoid risks of aggressiveness with respect to organic tissues.

In the embodiment illustrated in FIGS. 1 and 2, only the face 2a of the prosthetic plate 2 is surmounted by protuberances 3.

But especially in the case of reconstruction of hernias by surgery it can be preferred that the plate 1 be provided with anti-migratory protuberances on its two faces.

If the same technique ultrasound as hereinabove is to be conducted, the same tool can be used to form the annular zones and the protuberances on the two faces in two successive steps, the first to form the protuberances and the annular zones corresponding to said protuberances on one face and the second to form the protuberances and the corresponding annular zones on the other face, after the textile support is turned over.

FIG. 3 illustrates an embodiment of a prosthetic plate 11 whereof the textile support 12 is provided on its upper face 12a with protuberances 13. Each protuberance 13 is delimited by a peripheral portion 16 and comprises a central perforation 14. On its other internal face 12b this same prosthetic plate 11 comprises protuberances 23, delimited by a peripheral portion 26, shown in dotted lines in FIG. 3 and also comprising a central perforation 24. All these protuberances 13 and 23 are uniformly distributed in a stagger and alternating from one face 12a to the other 12b. In practice on the two faces 12a and 12b, the protuberances 13, 23 form parallel alignments both longitudinal and transversal, these alignments being offset from one face to the other by a distance which is equal to half the spread between two adjacent protuberances.

On the two faces 12a and 12b, the protuberances 13, 23 have substantially the same height h.

The peripheral annular portion 6, 16, 26 preferably has an inner diameter D which is of the order of 2 to 5 mm and a width l which is of the order of 0.5 mm.

FIG. 4 illustrates a plate 31 which comprises on its two faces protuberances 13, 23 identical to those of the example of FIG. 3. This prosthetic plate 31 further comprises radio-opaque marking 36 which is intended to enable radiological follow-up of the prosthetic plate 31 after its implantation. This follow-up must permit verification of the proper positioning of the plate during the period which precedes fixing by tissular colonisation. Also, due to the radio-opaque marking, checking the plate over time is made possible by taking comparative radiographs and measuring the intervals of the radio-opaque weft, in particular allowing evaluation of possible displacement of the plate as it ages. The radiological follow-up must also allowing marking of the placement of the plate for the purpose of a fresh operation on an other pathology requiring passage surgical by the zone where said plate is located. Finally, it must allow study, via simple and inexpensive examination, of the evolution of the textile support over time in terms of retraction and ageing, especially the comparative study of the radio-opaque weft in the event of recurrence, to better apprehend the cause.

The radio-opaque marking is in the form of lines 33, 34 to constitute a regular grid. The pitch P of the grid is between 2 and 45 mm, preferably of the order of 15 mm for a rectangular plate of 17 cm×15 cm. In the illustrated example in FIG. 4, the lines 33, 34 pass between the protuberances 13, 23, though this is not limiting.

Because of the arrangement of this marking in a regular grid, it is possible during radioscopic examination to verify if there is or not evolution in the distances separating the adjacent lines of the grid and consequently to notice any retraction of the textile support in which the plate is formed.

The radio-opaque marking as such can be obtained in particular by localised impregnation, according to the lines of the grid or according to any other pattern of the textile support (32), by a silicon composition comprising a radio-opaque charge, a charge which can especially be barium or tantalum sulphate.

In FIG. 4 the grid 32 is formed by longitudinal lines 33 and transversal lines 34, delimiting squares 35, each square containing one or two protuberances 13, 23. Also, the grid 32 occupies the entire surface of the plate 31. These particular arrangements are not exclusive, especially the grid which may occupy only part of the plate 31.

In a second embodiment, which will be described in reference to FIG. 5, the textile support 41 of the plate 40 is tissue of 3D or three-dimensional type, comprising two layers joined by connecting threads 42 obtained by knitting on a double-bed tricot machine. By way of non-limiting example, it has been made from polyester multi-filaments for two layers 43 and from polyester monofilaments for connecting threads 42. It presents a macroporous honeycomb structure, with hexagonal meshes forming regular openings or pores 44.

The technique of forming protuberances is the same as that which has been described hereinabove, with the exception that there are no perforations formed in the textile support 41 prior to formation of protuberances and thermowelding is applied to all fibres or filaments in the determined zone where the protuberance will be formed. This is produced by swaging and thermowelding by means of two complementary tools, male and female, having the preferred configuration for the protuberance, with or without a peripheral portion. Thermowelding is done by application of ultrasound treatment, by means of these two tools which in this case are sonotrodes, on the fibres or filaments which are deformed and compressed between the two male and female tools. In this case in the first instance there is deformation of the initial structure of the textile support, especially displacement of fibres or filaments relative to one another to produce the preferred configuration for the protuberance, and in the second instance there is thermowelding of fibres or filaments in their new arrangement. The at least superficial fusion of fibres or filaments developed during the thermowelding operation lends rigidity to the assembly of fibres or filaments of the protuberance, which increases its frictional properties and thus the anti-migratory character of the plate.

FIG. 5 clearly shows that the protuberance 45 comprises, on its substantially truncated wall, openings 46 which result at least in part from the deformation, especially the elongation, of the openings 44 existing in the structure of the 3D knitted fabric 41, deformation which occurs during swaging of said tricot 41 by the male slabbing tool. These openings 46 permit tissular colonisation of the plate 41 at the level of the protuberances 45 themselves, which are the plus immediately in contact with the organic tissues. Because of this, anchoring the plate 40 due to tissular colonisation proves more rapid than if this colonisation did not occur at the level of the protuberances 45 but only of the other openings 44 of the three-dimensional tricot 41. Not all protuberances necessarily comprise openings and the openings present in the protuberances do not all have the same size and the same configuration since this depends on the structure of the textile support in the determined zone in which the action of the slabbing tools for forming the protuberance occurs randomly.

The largest dimension of the openings in each protuberance can be of the order of 1 to 1.5 mm.

The above description has been only about the textile support 2, as an element forming the prosthetic plate. This is not exclusive. The textile support can comprise impregnation whereof the aim is to give the plate some shape memory, allowing it to be wound up on itself for introduction to a trocar and be deployed spontaneously when freed from the trocar. It can be impregnation of collagen, which has the advantage of accelerating tissular colonisation. It can also be impregnation of polyurethane.

The textile support can also comprise an anti-adherent coating on one of its faces, in particular on the face having no anti-migratory protuberances. Anti-adherent coating means a coating which is capable of preventing or at the very least substantially limiting adherences between the plate and those parts of the body against which it comes into contact, once implanted, especially the viscera. It can be a coating of collagen, polysaccharide or other biopolymer, resorbable or not.

In the event where the textile support is impregnated or comprises an anti-adherent coating, the formation of protuberances such as described hereinabove can occur either on the textile support alone prior to impregnation or prior to coating or respectively on the already impregnated textile support or on the textile support already covered in its coating.

The invention claimed is:

1. An implantable plate having first and second opposite faces for reconstruction of walls, comprising a textile support comprising fibers or filaments and having protuberances and a plane, said textile support is a three dimensional knit comprising two layers connected by connecting threads, wherein the protuberances are formed in at least one of the first and second faces of said textile support and protrude from said face(s), said protuberances are constituted of said fibers or filaments lending them an anti-migratory effect, wherein said protuberances have a conical or cylindrical configuration, and wherein the textile support is constituted at least in part by thermoplastic fibers or filaments and each protuberance is formed inside a determined zone of the textile support by deformation of the structure of the textile support and by pushing back said determined zone to the exterior of the plane of the textile support, and wherein said fibers or filaments surrounding said determined zone are thermowelded, but said fibers or filaments inside said determined zone are not thermowelded.

2. The plate as claimed in claim 1, wherein the textile support comprises perforations.

3. The plate as claimed in claim 2, wherein the perforations are centered relative to a peripheral portion of the determined zone, in which portion the fibers or filaments are thermowelded.

4. The plate as claimed in claim 3, wherein the peripheral portion is an annular portion having an inner diameter of the order of 2 to 5 mm and a width of the order of 0.5 mm.

5. The plate according to claim 2, wherein the perforations are arranged at the level of the protuberances.

6. The plate as claimed in claim 1, further comprising, on the first and second faces of the textile support, protuberances whereof the height is substantially equal to or greater than the thickness of said support, preferably less than three times said thickness, especially of the order of twice said thickness.

7. The plate as claimed in claim 1, further comprising protuberances, uniformly distributed in a stagger and alternating from the first face to the second face, at the rate of 0.5 to 2 protuberances per cm².

8. The plate as claimed in claim 1, wherein the textile support is tissue of 3D or three-dimensional type, comprising two layers connected by connecting threads, especially open tissue obtained by knitting on a double-bed warp machine.

9. The plate as claimed in claim 1, wherein at least some of the protuberances have openings, capable of allowing tissular colonisation of said protuberances.

10. The plate as claimed in claim 1, wherein the textile support is impregnated.

11. The plate according to claim 10, wherein the textile support is impregnated with collagen or polyurethane.

12. The plate as claimed in claim 1, wherein the textile support comprises on one of its faces an anti-adherent coating.

13. The plate according to claim 12, wherein the textile support comprises on the face not having an anti-migratory protuberance an anti-adherent coating.

14. The plate as claimed in claim 1, further comprising a radio-opaque marking on all or part of the surface of the textile support.

15. The plate as claimed in claim 14, wherein the marking is in the form of lines to constitute a regular grid having a pitch, the pitch of the grid being between 2 and 45 mm.

16. The plate according to claim 14, wherein the radio-opaque marking results from localised impregnation of the textile support by a silicon composition comprising a radio-opaque charge.

17. The plate according to claim 1, wherein each protuberance is formed by swaging and wherein all or part of said fibers or filaments are thermowelded by ultrasound.

18. An implantable plate having first and second opposite faces for reconstruction of walls, comprising a textile support comprising fibers or filaments and having protuberances and a plane, said textile support is a non-woven material which is thermobonded by points, wherein the protuberances are formed in at least one of the first and second faces of said textile support and protrude from said face(s), said protuberances are constituted of said fibers or filaments lending them an anti-migratory effect, wherein said protuberances have a conical or cylindrical configuration, and wherein the textile support comprises at least in part thermoplastic fibers or filaments and each protuberance is formed inside a determined zone of the textile support by deformation of the structure of the textile support and by pushing back said determined zone to the exterior of the plane of the textile support, and wherein said fibers or filaments surrounding said determined zone are thermowelded, but said fibers or filaments inside said determined zone are not thermowelded.

19. The plate as claimed in claim 18, wherein the textile support comprises perforations.

20. The plate as claimed in claim 18, wherein the perforation is centered relative to a peripheral portion of the determined zone in which portion the fibers or filaments are thermowelded.

\* \* \* \* \*